(12) United States Patent
Valentine et al.

(10) Patent No.: US 7,870,761 B2
(45) Date of Patent: Jan. 18, 2011

(54) GARMENT AND METHOD FOR PRODUCING THE SAME

(75) Inventors: Warren B. Valentine, London (GB); Abigaii Thomson, London (GB)

(73) Assignee: Koninklijke Philips Electronics N.V., Eindhoven (NL)

( * ) Notice: Subject to any disclaimer, the term of this patent is extended or adjusted under 35 U.S.C. 154(b) by 1122 days.

(21) Appl. No.: 10/513,942

(22) PCT Filed: May 5, 2003

(86) PCT No.: PCT/IB03/01867

§ 371 (c)(1),
(2), (4) Date: Nov. 9, 2004

(87) PCT Pub. No.: WO03/095020

PCT Pub. Date: Nov. 20, 2003

(65) Prior Publication Data

US 2006/0117805 A1    Jun. 8, 2006

(30) Foreign Application Priority Data

May 14, 2002    (GB) ................................ 0210889.2

(51) Int. Cl.
*D04B 1/22* (2006.01)
(52) U.S. Cl. ....................................................... 66/171
(58) Field of Classification Search ................... 66/170, 66/169 R, 171, 190
See application file for complete search history.

(56) References Cited

U.S. PATENT DOCUMENTS

| | | | |
|---|---|---|---|
| 4,016,868 A | | 4/1977 | Allison |
| 4,878,148 A | * | 10/1989 | Hee .............................. 66/193 |
| 5,078,134 A | | 1/1992 | Heilman et al. |
| 5,374,283 A | * | 12/1994 | Flick ............................ 607/46 |
| 6,047,203 A | * | 4/2000 | Sackner et al. .............. 600/388 |
| 6,145,551 A | * | 11/2000 | Jayaraman et al. ...... 139/387 R |
| 6,341,504 B1 | * | 1/2002 | Istook ....................... 66/172 E |
| 6,381,482 B1 | * | 4/2002 | Jayaraman et al. .......... 600/388 |
| 6,687,523 B1 | * | 2/2004 | Jayaramen et al. .......... 600/388 |
| 6,915,668 B2 | * | 7/2005 | Huang et al. .................. 66/171 |
| 6,970,731 B1 | * | 11/2005 | Jayaraman et al. .......... 600/388 |

FOREIGN PATENT DOCUMENTS

| | | | |
|---|---|---|---|
| FR | 2225560 A | * | 12/1974 |
| FR | 2737651 A1 | * | 2/1997 |
| JP | 11128187 | | 5/1999 |
| JP | 2003530184 | | 10/2003 |
| WO | WO9902052 | | 1/1999 |
| WO | WO9964657 | | 12/1999 |
| WO | WO0102052 | * | 1/2001 |
| WO | WO0178577 | | 10/2001 |

\* cited by examiner

*Primary Examiner*—Danny Worrell

(57) ABSTRACT

A garment includes a sensor band of generally smaller dimensions than the garment for holding sensor electrodes incorporated in the band against a user's body while wearing the garment. The sensor band is elasticated to conform against the user's body and the garment is relatively loose fitting. The sensor band may be attached to the remainder of the garment by highly elastic and flexible webbing portions.

19 Claims, 2 Drawing Sheets

GARMENT AND METHOD FOR PRODUCING THE SAME

The present invention relates to garments, in particular to garments assisting in the monitoring of a wearer, and methods for providing such garments.

WO-A-01/02052 describes a knitted garment comprising integral woven electrodes appropriately located such that when the garment is being worn the electrodes are positioned against a users skin to detect electrical signals associated with a user's heartbeat. Because the electrodes need to be maintained in contact against a user's skin, the garment itself needs to be close fitting. However, it is not always desirable that a garment is close fitting for one or a number of reasons. Tight fitting garments can become uncomfortable either because they are restrictive or because they cause covered areas of the skin to sweat more readily. Restrictive garments can be disadvantageous to performance where sporting activity is concerned. Furthermore, it may simply be a preferred option that a garment is relatively loose fitting rather than tight fitting, especially where such garments are traditionally of a loose fit.

In accordance with a first aspect of the present invention there is provided a garment provided with a sensor band for holding one or more sensor in contact with a wearer's body, said garment being provided with one or more linking portions extending from the garment and connected to the sensor band. Thus it is possible to provide a garment with an internal sensor band of smaller size than the external garment size thus allowing the internal sensor band to conform with a close fit to a wearer's skin while the remainder of the garment assumes a relative loose fit. In fact, it may not be readily apparent from the external appearance of the garment that a relatively tightly fitting component is present. Taking the example of the garment in the form of a tee shirt, held open out to form a generally cylindrical shape when viewed from above, the sensor band may have a diameter which is less than the diameter of other parts of the tee shirt that are intended to fit the torso.

The sensor band may be provided with one or more electrode. In this case, the one or each electrode may be integral with the sensor band. The one or each electrode may be of knitted construction. Preferably the sensor band includes resiliently extendable material allowing the band to stretch or contract to conform to the wearer's body. Preferably the linking portions are of high mechanical flexibility allowing the sensor band to conform to the user's body whilst simultaneously allowing minimal interference of movement between the sensor band and the remainder of the garment.

The garment may be formed as one common integral component, and where the garment is of a knitted construction a circular knitting technique may be employed. In this case it is possible to produce the whole garment or a major part of the garment with a single knitting process making efficient production possible with the minimum number of production stages. Such garments can also benefit in terms of look because there is an obviated or reduced need to sew together multiple components, thus allowing a simple, comfortable garment with no or few seams needing to be produced.

In accordance with a second aspect of the present invention there is provided a method of making a garment having the technical features of the garment of the first aspect of the present invention.

In accordance with a third aspect of the present invention there is provided a method of providing a garment of knitted construction, said method comprising the steps of;

performing a first knitting stage to produce a first garment portion;

performing a second knitting stage to produce a first mesh portion continuing from the first portion at a first interface;

performing a third knitting stage to produce a sensor band portion continuing from the first mesh portion at a second interface, the sensor band suitable for holding one or more sensor in contact with a wearer's body;

performing a fourth knitting stage to produce a second mesh portion continuing from the sensor band at a third interface; and performing a fifth knitting stage to produce a second garment portion continuing from the second mesh portion at a fourth interface.

Optionally, the method may further comprise the step of attaching the first interface to the fourth interface. In this case the step of attaching is optionally performed by a knitting process at commencement of performing the fifth knitting stage.

In accordance with a fourth aspect of the present invention, there is provided a method of providing a garment of knitted construction, said method comprising the steps of:

performing a first knitting stage to produce a first garment portion, performing a second knitting stage to produce a first mesh portion continuing from the first garment portion at a first interface; and performing a third knitting stage to produce a second garment portion continuing from the first mesh portion at a second interface.

Optionally, the method may further comprise the step of attaching the first interface to the second interface.

In this case the step of attaching is optionally performed by a knitting process at commencement of performing the third knitting stage.

The method of the fourth aspect of the present invention may also comprise the step of providing said first mesh portion with attachment means suitable for attaching with a sensor band capable of holding one or more sensor in contact with a wearer's body. Thus, sensor bands may be produced and supplied separately to the method of producing a garment according to the method of the fourth aspect.

In the case of each method of the present invention optionally at least one knitting stage employs a circular knitting technique.

These and other aspects of the present invention appear in the appended claims which are incorporated herein by reference and to which the reader is now referred.

The present invention will now be described with reference to the figures of the accompanying drawings in which.

Figure 1:
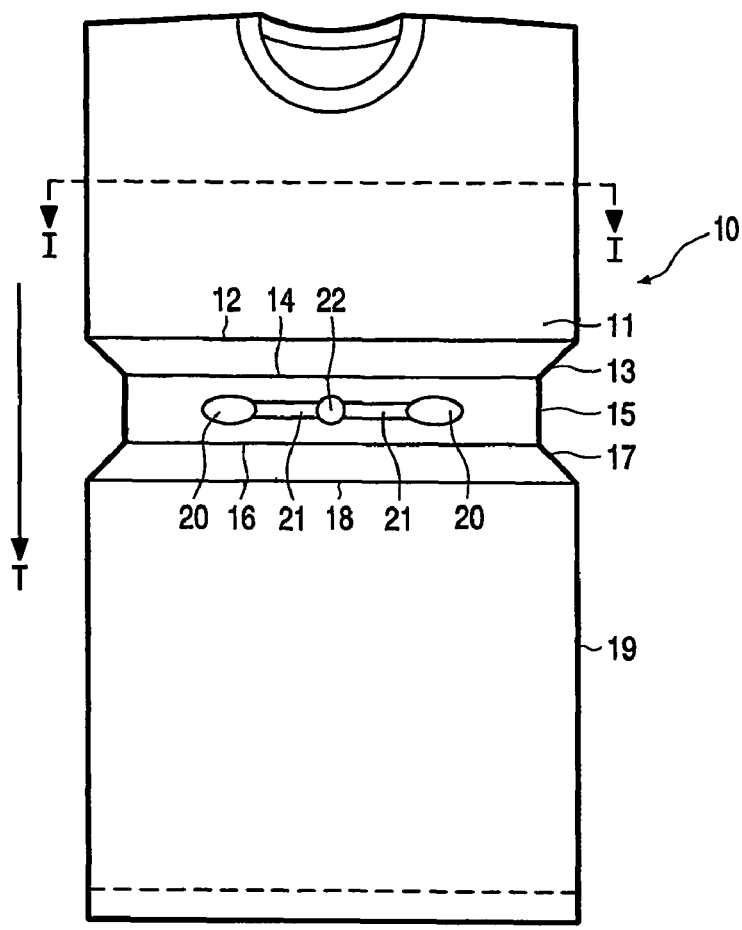
FIG. 1 shows a front view of a component suitable for forming a first embodiment of the present invention.
Figure 2:
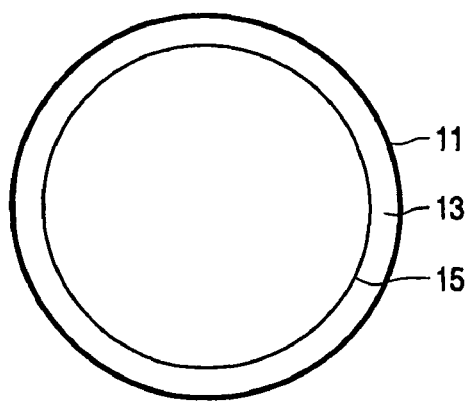
FIG. 2 is a cross sectional view taken along the line I-I of FIG. 1.

It should be noted that the drawings are diagrammatic and not drawn to scale. Relative dimensions and proportions of parts of the figures have been shown exaggerated or reduced in size for the sake of clarity and convenience in the drawings. The same reference signs are generally used to refer to corresponding or similar features in the different embodiments.

With reference to FIG. 1, a circular knitting technique is employed to produce a knitted component 10, the component being of generally, although not absolutely, tubular or cylindrical shape when considered when held open and viewed in the direction denoted 'T' in FIG. 1. The circular knitting technique is sometimes referred to as a seamless knitting technique. Although the construction is described as being generally tubular, the diameter of the construction can be varied as required at different regions by selectively using different stitch construction and/or by introducing resiliently extendible yarns (such as elastaine). The knit pattern may be controlled to produce openings, as may be used to provide armholes or a neck opening for example.

In one specific embodiment the component 10 is formed as one piece and comprises a first garment portion 11 of a first diameter which is produced by performing a first knitting stage starting at a first (top) end of the component and travelling in the direction denoted T. The portion 11 is produced until it extends to a first interface 12, where the first knitting stage ends and a second knitting stage begins, the second knitting stage serving to produce a first mesh portion 13 which extends from the first interface 12 to a second interface 14. The mesh portion provides a knit which is relatively lightweight in comparison with the first garment portion 11, the mesh portion being also highly flexible and capable of easily undergoing elastic deformation without application of much force. The mesh portion 13 is produced until it extends to the second interface 14, where the second knitting stage ends and a third knitting stage begins, the third knitting stage serving to produce a sensor band portion 15 which extends from the second interface 14 to a third interface 16. The sensor band is provided with integral knitted electrodes 20 arranged to face to the inside of the tube or cylinder formed by the component 10. The sensor band is also provided with conductive tracking 21 leading from each electrode 20 to a socket 22 suitable for receiving an electronic device and making electrical connection thereto. The sensor band (15) is of lesser diameter than the first garment portion 11 when considered in terms of the tube or cylinder formed by the component 10. The sensor band includes resilient extendible material, such as elastaine, so that the band may be enlarged through stretching in a radial direction on the application of force. The sensor band 15 is produced until it extends to the third interface 16, where the third knitting stage ends and a fourth knitting stage begins, the fourth knitting stage serving to produce a second mesh portion 17 which extends from the third interface 16 to a fourth interface 18. The second mesh portion 17 is of the same or similar material as the first mesh portion 13 and to has the same or similar characteristics. The second mesh portion 17 is produced until it extends to the fourth interface 18, where the fourth knitting stage ends and a fifth knitting stage begins, the fifth knitting stage serving to produce a second garment portion 19 which extends from the fourth interface 18 to a second (bottom) end of the component 10. The second garment portion is of generally the same dimensions as the first garment portion.

The first interface 12 is joined to the fourth interface 18. This may be done by sewing. Alternatively this may be done as a part of the knitting process while producing the component 10. In this case, the knitting machine would maintain a set of needles engaged with the component 10 in the vicinity of the first interface and once the fourth knitting stage had been completed but as the fifth knitting stage is commenced, the machine would return to the vicinity of the first interface to connect the component at the first and fourth interface using the knitting process.

Figure 3:
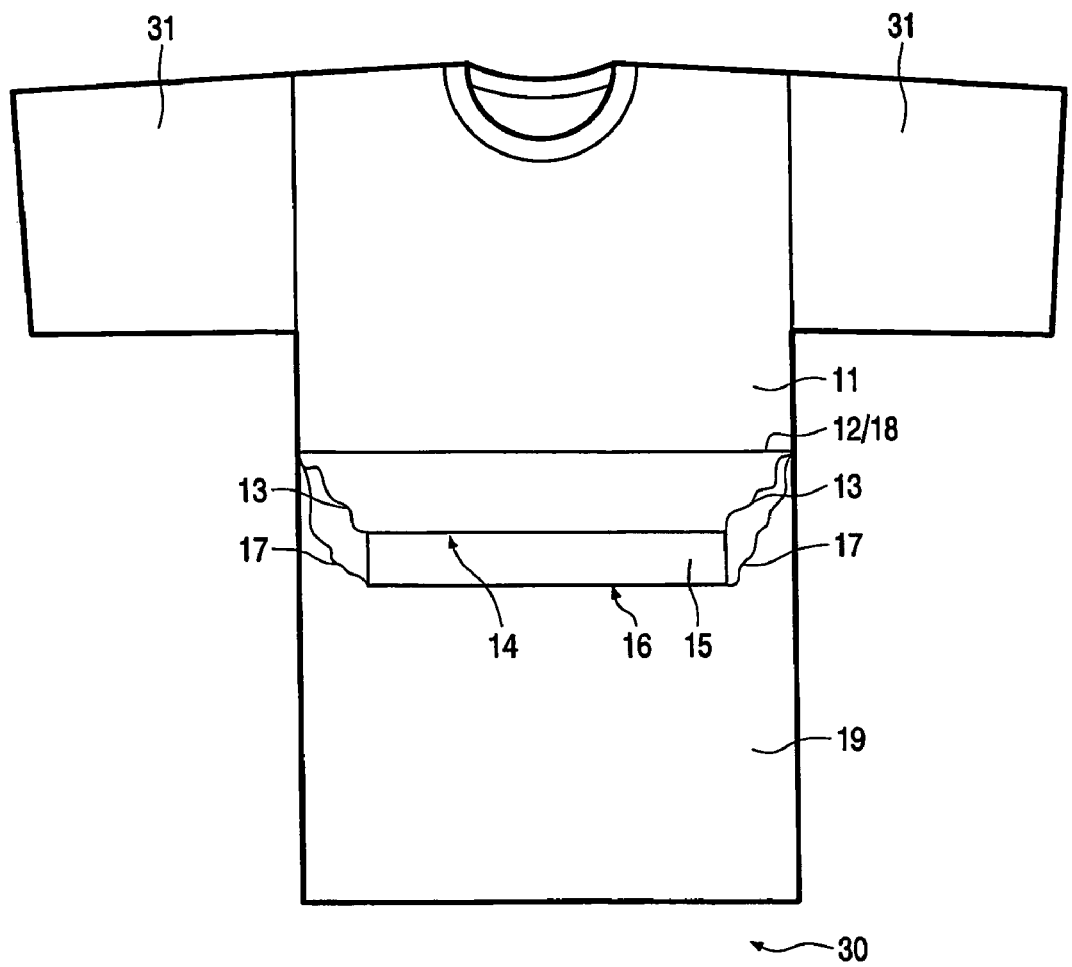
FIG. 3 is a cross sectional view of a first embodiment of the present invention.

FIG. 3 shows the completed garment in the form of a t-shirt 30, with additional sleeve portions 31 added, attached by sewing or the like. The sensor band 15 is of smaller diameter than the first and second garment portions 11, 19, the sensor band being suspended by flexible mesh portions 13, 17 that extend inwardly toward a wearer's body from the inner surface of the garment. When this garment is produced at a size appropriate for a wearer, the t-shirt garment portions 11, 19 will be of relatively loose comfortable fit to the user while the sensor band portion 15 stretches to form a conforming fit around the torso of the body and maintain sensor electrodes 20 in contact with the skin. Such sensor electrodes can detect electrical signals associated with users heartbeat. These signals can be communicated along conductive tracking 21 to electronic equipment accommodated in socket opening 22.

Thus it is possible to provide a garment which allows sensor electrodes to be held against the body while also providing a garment which is generally of a relatively loose fit, thereby contributing to comfort of the user.

While the present embodiment is shown as a tee-shirt, other arrangements will be apparent to the person skilled in the art, such as providing a garment of the present invention in other forms, for example as a pair of trousers with sensor bands. Although the sensor band is described as being provided with electrodes, other components may be accommodated by the sensor band, in addition to or instead of the described electrodes. These other components include further sensing electrodes, stretch/expansion sensors, temperature sensors, perspiration sensors or other sensors for performing measurements on a wearer's body or their immediate surroundings. Furthermore, although the garment is said to be provided with a sensor band, it will be appreciated by the person skilled in the art that the sensor band may accommodate components which do not behave as sensors (input devices) but as output devices, such as electrodes for application of electric potential to a wearer. Thus a sensor band with the general mechanical functionality as described herein but accommodating input and output devices or only output devices should still be viewed as a sensor band that falls within the scope of the claims and so a garment having such a sensor band may be produced which falls within the scope of the present invention.

The described embodiment has a sensor band permanently in place. However, sensor bands may be made and produced separately so that they may be interchangeable. However, in some designs it will be possible for sensor bands to be removably attached to the garment. This will permit a sensor band having different functionality to be introduced in a garment. Alternatively a sensor band may be removed for cleaning e.g. washing. Furthermore, where a sensor band has a shorter lifetime than the remainder of the garment, a new sensor band may be exchanged for an old sensor band, thereby extending the overall lifetime of the garment. In this arrangement some means need to be provided for removably attaching the sensor band to the rest of the garment, such means including any suitable fastening means, such as VELCRO™ (a brand name of fabric hook-and-loop fasteners used for connecting objects), press-studs and zippers, as will be appreciated by the person skilled in the art. Slight modifications may be necessary for implementing this arrangement; for example the first and second mesh portions join each other to form one mesh portion without there being an intermediate sensor band, and this mesh portion is provided with fastening means for attaching a sensor band. In another arrangement the mesh portions are permanently attached to a sensor band and thus replaced as the sensor band is replaced. In this case the mesh portions are provided with fastening means to removably attach the mesh portions with the remainder of the garment, for example first garment portion 11 and second garment portion 19. However, in this latter arrangement a single garment portion could theoretically replace first and second garment portions 11, 19. The remainder of the garment has fastening means to co-operate with the fastening means of the mesh portions.

From reading the present disclosure, other modifications will be apparent to the person skilled in the art. Such modifications may involve other features which are already known in the design and manufacture and use of garments, clothing accessories, health monitoring or treatment devices, sports training products, wearable computer arrangements and applications thereof, and thus may be used instead of or in addition to features already described herein.

The invention claimed is:

1. A garment comprising:
 a sensor band for holding one or more sensors in contact with a wearer's body, and
 a plurality of linking portions connected to the sensor band at first interfaces and to the garment at second interfaces, wherein the second interfaces are joined together so that the linking portions and the sensor band are inside the garment, and
 wherein a diameter of the sensor band is smaller than a diameter of a portion of the garment where the sensor band is attached to the garment via the linking portions.

2. The garment in accordance with claim 1 wherein said sensor band is provided with one or more electrodes.

3. The garment in accordance with claim 2 wherein the one or more electrodes is integral with the sensor band.

4. The garment in accordance with claim 2 or 3 wherein the one or more electrodes is of knitted construction.

5. The garment in accordance with claim 1, wherein said sensor band includes resiliently extendable material allowing the sensor band to stretch or contract to conform to the wearer's body.

6. The garment in accordance with claim 1, wherein the plurality of linking portions are of a highly mechanically yielding material.

7. The garment in accordance with claim 1, wherein the garment is of knitted construction.

8. The garment in accordance with claim 7 wherein the garment and the plurality of linking portions are formed as a common integral component.

9. The garment in accordance with claim 7 wherein the garment, the plurality of linking portions and the sensor band are formed as a common integral component.

10. The garment in accordance with claim 1, wherein the garment is made using a circular knitting technique.

11. A method of providing a garment of knitted construction, said method comprising the acts of:
 performing a first knitting stage to produce a first garment portion,
 performing a second knitting stage to produce a first mesh portion continuing from the first garment portion at a first interface;
 performing a third knitting stage to produce a sensor band continuing from the first mesh portion at a second interface;
 performing a fourth knitting stage to produce a second mesh portion continuing from the sensor band at a third mesh portion;
 performing a fifth knitting stage to produce a second garment portion continuing from the second mesh portion at a fourth mesh portion; and
 joining the first interface and the fourth interface so that the first mesh portion, the second mesh portion, and the sensor band are inside the garment,
 wherein the sensor band contacts a wearer's body.

12. The method in accordance with claim 11 and further comprising the act of providing said first mesh portion with attachment means suitable for attaching with the sensor band which is capable of holding one or more sensors in contact with a wearer's body.

13. The garment of claim 1, wherein the sensor band is removably attachable to the plurality of linking portions.

14. The method of claim 11, wherein a diameter of the sensor band is smaller than a diameter of the first garment portion where the sensor band is attached to the garment.

15. A garment comprising:
 a sensor band for holding one or more sensors in contact with a wearer's body; and
 a plurality of linking portions connected to the sensor band at first interfaces and to the garment at second interfaces, wherein the second interfaces are joined together so that the linking portions and the sensor band are inside the garment.

16. The garment of claim 15, wherein the sensor band comprises a flexible material and wherein a diameter of the sensor band is smaller than a diameter of a portion of the garment where the sensor band is attached to the garment via the linking portions.

17. The garment of claim 15, wherein the sensors are adapted to detect electrical signals associated with the wearer's heartbeat.

18. The garment of claim 15, wherein the sensor band comprises a socket adapted for connecting with an electrical device, and wherein the sensors are in electrical contact with the socket via conductive tracking formed along the sensor band.

19. The garment of claim 15, wherein the linking portions have dimensions and comprise a material that allow the sensor band to maintain the sensors in contact with the wearer's body while a portion of the garment that is laterally outward from the sensor band is separated from the wearer's body.

* * * * *